US008876911B2

(12) United States Patent
Murphy et al.

(10) Patent No.: US 8,876,911 B2
(45) Date of Patent: *Nov. 4, 2014

(54) DELIVERY DEVICE FOR BIOLOGICAL COMPOSITES AND METHOD OF PREPARATION THEREOF

(75) Inventors: James P. Murphy, Newtown Square, PA (US); Charanpreet S. Bagga, Phoenixville, PA (US); Robert J. Chiasera, Jr., Parkesburg, PA (US); Erik M. Erbe, Berwyn, PA (US); Jeffrey G. Marx, Downingtown, PA (US)

(73) Assignee: Orthovita, Inc., Malvern, PA (US)

( * ) Notice: Subject to any disclaimer, the term of this patent is extended or adjusted under 35 U.S.C. 154(b) by 1180 days.

This patent is subject to a terminal disclaimer.

(21) Appl. No.: 11/384,576

(22) Filed: Mar. 20, 2006

(65) Prior Publication Data

US 2006/0184131 A1    Aug. 17, 2006

Related U.S. Application Data

(63) Continuation of application No. 10/818,419, filed on Apr. 5, 2004, now Pat. No. 7,052,517, which is a continuation-in-part of application No. 09/939,505, filed on Aug. 24, 2001, now Pat. No. 6,736,799.

(60) Provisional application No. 60/242,906, filed on Oct. 24, 2000.

(51) Int. Cl.
| A61M 31/00 | (2006.01) |
| A61F 2/28 | (2006.01) |
| A61L 27/46 | (2006.01) |
| A61L 27/56 | (2006.01) |
| A61L 27/54 | (2006.01) |
| A61B 17/88 | (2006.01) |
| A61M 25/00 | (2006.01) |
| A61M 5/34 | (2006.01) |

(52) U.S. Cl.
CPC ............ *A61L 27/46* (2013.01); *A61M 25/0097* (2013.01); *A61L 2300/00* (2013.01); *A61M 5/34* (2013.01); *A61L 27/56* (2013.01); *A61L 27/54* (2013.01); *A61B 17/8825* (2013.01); *A61B 17/8816* (2013.01)
USPC ............................................ 623/23.61; 604/60

(58) Field of Classification Search
USPC ............. 604/181, 23.51, 23.55, 23.56, 23.58, 604/23.61, 23.62, 57, 59–64; 523/115, 116; 428/404; 427/2.26, 2.27; 423/305, 311; 623/23.51, 23.55, 23.56, 23.58, 23.61, 623/23.62
See application file for complete search history.

(56) References Cited

U.S. PATENT DOCUMENTS

| 3,090,094 A | 5/1963 | Schwartzwalder et al. ..... 25/156 |
| 3,679,360 A | 7/1972 | Rubin et al. .................... 23/109 |

(Continued)

FOREIGN PATENT DOCUMENTS

| EP | 0 263 489 A1 | 4/1988 |
| EP | 0 417 493 A2 | 3/1991 |
| GB | 2260538 | 4/1993 |

OTHER PUBLICATIONS

Abbona, F., et al., "Crystallization of calcium and magnesium phosphates from solutions of medium and low concentrations," *Cryst. Res. Technol.*, 1992, 27, 41-48.

(Continued)

*Primary Examiner* — Aarti B Berdichevsky
*Assistant Examiner* — Bradley Osinski
(74) *Attorney, Agent, or Firm* — Lerner, David, Littenberg, Krumholz & Mentlik, LLP

(57) ABSTRACT

An apparatus for the delivery of a biological composite and a method, kit, and system for preparing a biological composite is described herein. The biological composite includes both inorganic and biological materials.

19 Claims, 11 Drawing Sheets

(56) References Cited

U.S. PATENT DOCUMENTS

| | | | | |
|---|---|---|---|---|
| 3,833,386 | A | 9/1974 | Wood et al. | 106/41 |
| 3,877,973 | A | 4/1975 | Ravault | 264/44 |
| 3,907,579 | A | 9/1975 | Ravault | 106/41 |
| 4,004,933 | A | 1/1977 | Ravault | 106/40 R |
| 4,007,020 | A | 2/1977 | Church et al. | 51/205 |
| 4,045,238 | A | 8/1977 | Battista et al. | 106/122 |
| 4,065,360 | A * | 12/1977 | Kreb, III | 600/578 |
| 4,149,893 | A | 4/1979 | Aoki et al. | 106/35 |
| 4,328,034 | A | 5/1982 | Ferguson | 106/75 |
| 4,551,135 | A | 11/1985 | Gorman et al. | 604/82 |
| 4,612,053 | A | 9/1986 | Brown et al. | 706/35 |
| 4,613,627 | A | 9/1986 | Sherman et al. | 521/68 |
| 4,664,128 | A * | 5/1987 | Lee | 600/566 |
| 4,673,355 | A | 6/1987 | Farris et al. | 433/218 |
| 4,781,721 | A | 11/1988 | Grundei | 623/16 |
| 4,801,263 | A | 1/1989 | Clark | 433/90 |
| 4,849,193 | A | 7/1989 | Palmer et al. | 423/308 |
| 4,859,383 | A | 8/1989 | Dillon | 264/43 |
| 4,861,733 | A | 8/1989 | White | 501/1 |
| 4,880,610 | A | 11/1989 | Constantz | 423/305 |
| 4,897,250 | A | 1/1990 | Sumita | 423/308 |
| 4,927,866 | A | 5/1990 | Purrmann et al. | 523/115 |
| 4,983,573 | A | 1/1991 | Bolt et al. | 505/1 |
| 5,034,352 | A | 7/1991 | Vit et al. | 501/1 |
| 5,047,031 | A * | 9/1991 | Constantz | 606/77 |
| 5,112,354 | A | 5/1992 | Sires | 623/16 |
| 5,129,905 | A | 7/1992 | Constantz | 606/76 |
| 5,133,703 | A * | 7/1992 | Boehringer et al. | 604/317 |
| 5,134,009 | A | 7/1992 | Ichitsuka et al. | 428/113 |
| 5,219,829 | A | 6/1993 | Bauer et al. | 505/1 |
| 5,296,261 | A | 3/1994 | Bouet et al. | 427/123 |
| 5,298,205 | A | 3/1994 | Hayes et al. | 264/25 |
| 5,322,675 | A | 6/1994 | Hakamatsuka et al. | 423/311 |
| 5,338,334 | A | 8/1994 | Zhen et al. | 75/362 |
| 5,338,356 | A | 8/1994 | Hirano et al. | 106/690 |
| 5,409,982 | A | 4/1995 | Imura et al. | 524/417 |
| 5,427,754 | A | 6/1995 | Nagata et al. | 423/308 |
| 5,435,844 | A | 7/1995 | Sasaya | 106/122 |
| 5,496,399 | A | 3/1996 | Ison et al. | 106/35 |
| 5,522,893 | A | 6/1996 | Chow et al. | 623/11 |
| 5,525,148 | A | 6/1996 | Chow et al. | 106/35 |
| 5,531,255 | A * | 7/1996 | Vacca | 141/285 |
| 5,545,254 | A | 8/1996 | Chow et al. | 106/35 |
| 5,645,934 | A | 7/1997 | Marcolongo et al. | 428/357 |
| 5,660,778 | A | 8/1997 | Ketcham et al. | 264/630 |
| 5,681,872 | A | 10/1997 | Erbe | 523/114 |
| 5,772,665 | A | 6/1998 | Glad et al. | 604/82 |
| 5,824,084 | A | 10/1998 | Muschler | 623/16 |
| 5,914,356 | A | 6/1999 | Erbe | 523/114 |
| 5,939,039 | A | 8/1999 | Sapieszko et al. | 423/311 |
| 6,049,026 | A | 4/2000 | Muschler | 623/16 |
| 6,136,029 | A | 10/2000 | Johnson et al. | |
| 6,325,987 | B1 | 12/2001 | Sapieszko et al. | 423/305 |
| 6,383,519 | B1 | 5/2002 | Sapieszko et al. | 424/489 |
| 6,458,162 | B1 | 10/2002 | Koblish et al. | 623/23.51 |
| 6,544,290 | B1 * | 4/2003 | Lee et al. | 623/23.63 |
| 6,736,799 | B1 | 5/2004 | Erbe et al. | 604/181 |
| 7,045,125 | B2 | 5/2006 | Erbe et al. | 424/93.7 |
| 2002/0127720 | A1 | 9/2002 | Erbe et al. | 435/395 |
| 2004/0254538 | A1 * | 12/2004 | Murphy et al. | 604/181 |

OTHER PUBLICATIONS

Brown, P.W., et al., "Variations in solution chemistry during the low temperature formation of hydroxapaptite," *J. Am. Ceram. Soc.*, 1991, 74(8), 1848-1854.

Chaair H., et al., "Precipitation of stoichiometric apatitic tricalcium phosphate prepared by a continuous process," *J. Mater. Chem.*, 1995, 5(6), 895-899.

Driessens, F.C.M., et al., "Effective formulations for the preparation of calcium phosphate bone cements," *J. Mat. Sci.: Mat. Med.*, 1994, 5, 164-170.

Famery, R., et al.; "Preparation of alpha-and beta-tricalcium phosphate ceramics, with and without magnesium addition," *Ceram. Int.*, 1994, 20, 327-336.

Fukase, Y., et al., "Setting reactions and compressive strengths of calcium phosphate cements,"*J. Dent. Res.*, 1990, 69(12), 1852-1856.

Greenwood, N.N., et al., "Oxoacids of phosphorus and their salts," in *Chemistry of the Elements, Pergamon Press*, 1984, 586-595.

Ishikawa, K., et al., "Properties and mechanisms of fast-setting calcium phosphate cements,"*J. Mat. Sci.: Mat. Med.*, 1995, 6, 528-533.

Kingery, W.D., et al.(Eds.), Introduction to Ceramics, $2^{nd}$ Ed., *John Wiley & Sons*, 1960, 416.

Koutsoukos, P., et al., "Crystallization of calcium phosphates. A constant composition study," *J. Am. Chem. Soc.*, 1980, 102, 1553-1557.

Lacout, J.L., "Calcium phosphate as bioceramics," in *Hart Tissue Repair and Replacement*, Elsevier Science Publishers, 1992, 81-95.

LeGeros, R.Z., "Calcium phosphates in oral biology and medicine," *Monographs in Oral Science*, Meyers, H.M. (Ed.), Karger Press, 1991, 15, 108-129.

LeGeros, R.Z., "Biodegradation and bioresorption of calcium phosphate ceramics," *Clin. Mat*, 1993, 14(1), 65-88.

LeGeros, R.Z., "Preparation of octacalcium phosphate (OCP): A direct fast method," *calcify. Tiss. Int.*, 1985, 37,194-197.

Mirtchi, A., et al., "Calcium phosphate cements: effect of fluorides on the setting and hardening of beta-tricalcium phosphate—dicalcium phosphate—calcite cements," *Biomat.*, 1991, 12, 505-510.

Monma, H., et al., "properties of hydroxyapatite prepared by the hydrolysis of tricalcium phosphate," *J. Chem. Tech. Biotechnol.*, 1981, 31, 15-24.

Nancollas, G.H., "The involvement of calcium phosphates in biological mineralization and demineralization processes," *Pure Appl. Chem.*, 1992, 64(11), 1673-1678.

Nancollas, G.H., "In vitro studies of calcium phosphate crystallization," in *Biomineralization Chemical and Biochemical Perspectives*, 1989, 157-187.

Nancollas, G.H., et al., "Formation and dissolution mechanisms of calcium phosphates in aqueous systems," in *Hydroxyapatite and Related materials*, CRC Press., Inc., 1994, 73-81.

Powell, S.J., et al., "The structure of ceramic foams prepared from polyurethane-ceramic suspension," *Materials & Manuf. Processes*, 1995, 10(4), 757-771.

Vereecke, G., et al., "Calculation of the solubility diagrams in the system $Ca(OH)_2$—$H_3PO_4$—KOH—$HNO_3$—$CO_2$—$H_2O$," *J. Cryst. Growth*, 1990, 104, 820-832.

Wong, A.T.C., et al., "Prediction of precipitation and transformation behavior of calcium phosphate in aqueous media," in *Hydroxyapatite and Related Materials*, Brown, P.W., et al., (Eds.), CRC Press, Inc., 1994, 189-196.

* cited by examiner

120

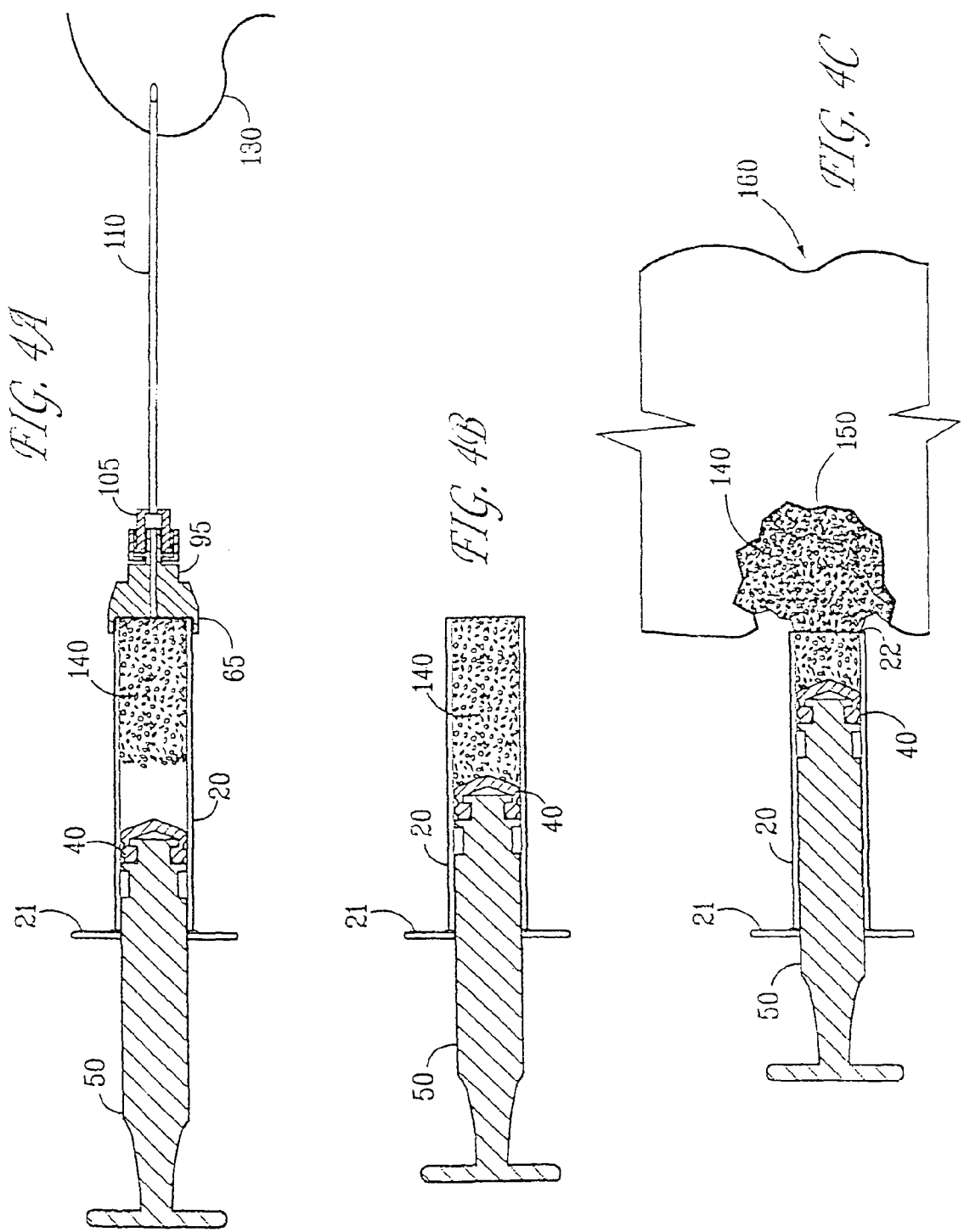

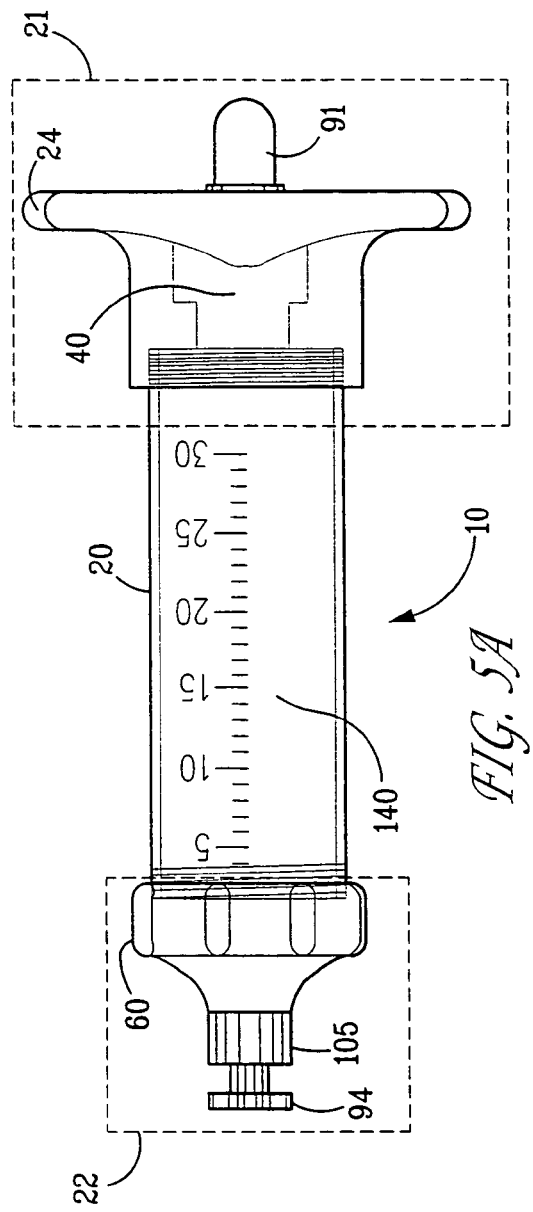
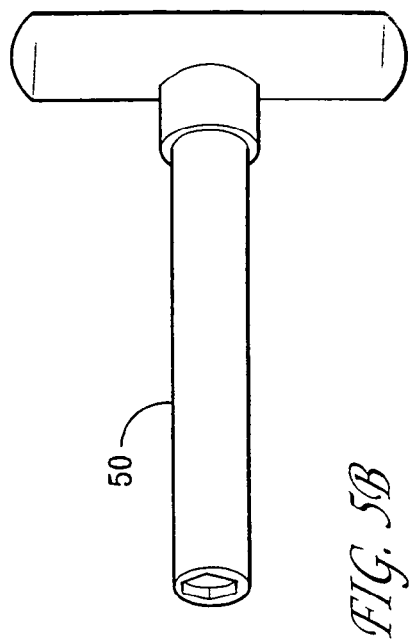
FIG. 5A
FIG. 5B

DELIVERY DEVICE FOR BIOLOGICAL COMPOSITES AND METHOD OF PREPARATION THEREOF

CROSS REFERENCE TO RELATED APPLICATIONS

This application is a continuation of U.S. application Ser. No. 10/818,419 filed Apr. 5, 2004, which is a continuation-in-part of U.S. application Ser. No. 09/939,505, U.S. Pat. No. 6,736,799, filed Aug. 24, 2001, which claims benefit under 119 (c) priority to U.S. Application No. 60/242,906 filed Oct. 24, 2000, each of which is incorporated herein by reference in its entirety.

FIELD OF THE INVENTION

The present invention generally relates to apparatuses for the delivery of biological composites that facilitate imbibation and infiltration of porous substrates with biological materials to form biological composites, together with kits comprising the same. This application also relates to methods for the preparation and delivery of biologically active composites that may comprise both a substrate material and biological materials. The biological composites preferably comprise an inorganic substrate, such as for example, a calcium phosphate inorganic material like beta-tricalcium phosphate ("β-TCP"), and a biological component, such as for example, bone marrow aspirate ("BMA").

BACKGROUND OF THE INVENTION

When bone integrity is threatened by surgical procedure, trauma, infection, congenital malformation, tumor growth, or degenerative diseases bone grafting can be used to encourage the affected bone to regenerate and heal. A bone graft functions like cancellous bone because it supports new tissue growth by providing the bone and blood cells with a matrix through which to interweave as the bone and blood cells reconnect bone fragments. For a bone graft to be successful, three processes that mimic natural events in cancellous bone should take place: osteoinduction, osteogenesis, and osteoconduction. Osteoinduction is the biologically mediated recruitment and differentiation of cell types essential for bone. Osteogenesis is the process of bone formation through cellular osteoblastic activity, which is dependent upon the presence of osteoprogenitor stem cells. Lastly, osteoconduction is the apposition of growing bone to the three-dimensional surface of a suitable scaffold provided by the graft.

Orthopedists are currently using a variety of materials that enhance, to various degrees, these three processes. The basic types of bone substitutes, which are sometimes used alone and sometimes in combination, comprise the autograft, cadaveric allograft, xenograft, and several types of graft materials.

Ideally, materials used for bone grafts will provide for osteogenesis, osteoinduction, and osteoconduction, resulting in vigorous new bone growth that will repair the defect. One effective bone graft material in current use is the autogenous cancellous bone graft. However, survival of intrinsic osteogenic stem cells in the autograft is not optimal, and the harvesting process (generally from the iliac crest) results in considerable pain and morbidity to the patient. As a result, alternative bone-grafting strategies have been investigated. The development of composite grafts that combine synthetic or partially synthetic cancellous bone void fillers with autogenous bone-forming cells could simplify and improve grafting procedures.

There have been devices in the art which allow for the mixing of bodily fluids within a syringe comprising inorganic particles and morsels. Few of these devices, however, provide a device that allows for the formation of a biologically active composite capable of fostering osteoinduction, osteogenesis, and osteoconduction.

For example, U.S. Pat. No. 4,551,135 ("Gorman"), incorporated herein by reference in its entirety, discloses a syringe for the extrusion of a semi-plastic mass. This dispensing syringe has a barrel which may be pre-loaded with a semi-plastic mass or one component of a multi-component plasticizable mixture. Fluid may be injected into the syringe to add a liquid component to the dispensing syringe. Since the liquid component is injected into the dispensing syringe, the Gorman device has a structural limitation that calls for a vent hole. It appears that it is not foreseen that such a device may be used to mix a fluid and a mass using vacuum pressure or suction.

U.S. Pat. No. 4,065,360 ("Kreb"), incorporated herein by reference in its entirety, discloses a syringe device for drawing fluids directly into cavities that can be sealed by the syringe's piston. The syringe includes a hollow housing, a movable piston, at least one culture cavity in the walls of the housing, and a sealing means about the periphery of the movable piston. Fluid is drawn into the cavities when the piston is moved outward from the housing. Once the piston is moved inward, the cavities are sealed and the fluid is allowed to intermix with whatever culture medium is chosen. In this device, however, the cavities are separate from the material chamber and the fluid and medium are only allowed to mix when the piston is closed. This also only allows for a relatively small amount of material to be imbibed by the syringe.

U.S. Pat. No. 4,801,263 ("Clark"), incorporated herein by reference in its entirety, discloses a device for placing osseous implant substances into interdental alveolar bone defects. The device includes a syringe barrel, a syringe plunger member having a piston rod, grasping members attached to an external surface of the syringe barrel, and a threaded nozzle coupler attached to the exterior of the barrel member for allowing an extended nozzle member to be attached to the syringe barrel. This device, however, is incapable of housing a composite and simultaneously imbibing the composite with a fluid.

U.S. Pat. No. 5,772,665 ("Glad"), incorporated herein by reference in its entirety, discloses a device for mixing a pharmaceutical composition and storage for an extended period. The device has a hollow body having an outlet sealed by a removable closure, a plunger within the hollow body, and a chamber for housing the pharmaceutical composition. Fluid can be added to the chamber by withdrawing the plunger upward and allowing water to enter through the lower end or by placing the lid on the lower end, removing the plunger and pouring/injecting water into the upper opening. When the filling is complete, either the lid is applied to the lower end or the plunger is re-inserted into the hollow body, respectively. However, in one embodiment, the lower end of this device is not a syringe tip and one could not use it to aspirate material held within its chamber with fluids drawn directly from the body. In a second embodiment where an injection needle may be fitted onto the Luer cone, the device is incapable of containing a composite that fills the material chamber and then aspirating that composite via vacuum infiltration with bodily fluids without the use of its plunger because the non dispensing end is a handle attached to an actuating rod. It cannot accommodate a secondary needle or vacuum pump.

U.S. Pat. Nos. 5,824,084 and 6,049,026 (referred to herein collectively as "Muschler") disclose a method of preparing a composite bone graft and apparatus for preparing an implantable graft, respectively, which includes a porous, biocompatible, implantable substrate, a container for retaining the substrate and for permitting flow of a bone marrow aspirate suspension (bone marrow aspirate that may include an isotonic solution and an anti-coagulant) completely through the substrate into an effluent container for receiving effluent of the bone marrow aspirate suspension from the container. Muschler also teaches a graft having an enriched population of connective tissue progenitor cells, the graft being the resultant product of the disclosed method and apparatus.

There is a need to provide for the formation and delivery of a highly porous, inorganic substrate that is rendered biologically active by the aspiration of a biological material into the device. Further, there is a need in the art to provide a method for restoring an osseous void that may be employed in situations that require the use of a bone void filler for filling voids or gaps that are not intrinsic to the stability of the bony structure of the skeletal system. Moreover, there is a need in the art to provide a kit that can form a biologically active composite and deliver the composite mass into an osseous void thereby restoring the void.

SUMMARY OF THE INVENTION

The present invention provides an apparatus capable of housing a substrate material. The material is infiltrated with a biological substance to provide a biological composite. In one embodiment, the present invention provides an apparatus for preparing a biological composite comprising a material chamber, having a proximal end and a distal end, containing a calcium phosphate material having macro-, meso- and micro-porosity, the proximal end being sealingly closed by a movable plunger; and the distal end of the chamber being closed by a dismountable end cap, the end cap being provided with a point for attachment of an aspiration needle. In certain embodiments, the apparatus further comprises a closed end cap that is interchangeable with the dismountable end cap for sealing the material chamber between the plunger and the closed end cap.

In another embodiment of the present invention, there is provided a method for preparing a biological composite comprising the steps of: providing an apparatus comprising a material chamber comprising an inorganic, biologically compatible material having macro-, meso- and micro-porosity and having a proximal end and a distal end, the proximal end being sealingly closed by a movable plunger; the distal end of the chamber being closed by a dismountable end cap, the end cap being provided with a point for attachment of an aspiration needle; attaching the aspiration needle to the dismountable end cap; placing the aspiration needle into a situs of bone marrow; operating the plunger to draw a partial vacuum in the material chamber and to cause aspiration of bone marrow into the material chamber in an amount sufficient to substantially wet the biologically compatible morselate material; and maintaining the aspirate in contact with the biologically compatible composite under conditions effective to cause at least partial coalescence of the marrow-morselate mixture. In one embodiment, the inorganic material is a highly porous β-TCP material with a pore volume of at least 70% and interconnected micro-, meso-, and macro-porosity; and the biological material is bone marrow aspirate. In another embodiment, the material is a highly porous composite of a porous β-TCP material and an organic polymer, such as collagen with a pore volume of at least 70% and interconnected micro-, meso-, and macro-porosity.

In a further embodiment of the present invention, there is provided a kit for the preparation and delivery of biologically active composites comprising an instrument for the injection and the withdrawal of one or more biological fluids and a porous, biocompatible material wherein the porous, biocompatible material comprises interconnected micro-, meso- and macro-porosity.

It will be appreciated that further embodiments of the present invention may be developed from this disclosure. For instance, disclosed herein are apparatuses for preparing a biological composite, comprising a plunger having tabs for mating; a material cartridge comprising a chamber having a proximal end and a distal end and, within said chamber, calcium phosphate material having macro-, meso- and micro-porosity, the proximal end having a piston for mating with said plunger; and the distal end of the chamber being closed by a dismountable end cap, the end cap being provided with a point for attachment of an aspiration needle. The apparatuses may further comprise two seals located on either end of said material chamber adjacent to said piston and said end cap. Other embodiments may further comprise a vacuum adapter connected to said proximal end. The biocompatible material used may also comprise structural proteins such as collagen.

Methods for preparing biological composites are also disclosed. These methods comprise the steps of:

- providing an apparatus comprising a plunger having a means for mating; a material cartridge comprising a chamber having a proximal end and a distal end, and, within said chamber, calcium phosphate material having macro-, meso- and micro-porosity, the proximal end having a piston for mating with said plunger means; the distal end of the chamber being closed by a dismountable end cap, the end cap being provided with a point for attachment of an aspiration needle;
- placing the aspiration needle into a situs of bone marrow or blood pathway;
- attaching the aspiration needle to the dismountable end cap;
- drawing a vacuum in the material chamber to cause aspiration of bone marrow into the material chamber in an amount sufficient to substantially wet the biologically compatible material to form a biologically compatible composite; and
- maintaining the aspirate in contact with the biologically compatible composite under conditions effective to cause at least partial coalescence of the marrow within the composite.

In some embodiments of the disclosed methods, the step of drawing a vacuum may comprise attaching a second piston syringe to the proximal end of said material chamber; and operating said second syringe to draw a vacuum in the material chamber. In other embodiments, the methods further comprise the step of attaching a vacuum line adaptor to the proximal end of said material chamber; and operating the vacuum line adaptor to draw a vacuum in the material chamber.

These and other aspects of the invention will be apparent from the following drawings and detailed description of preferred embodiments.

BRIEF DESCRIPTION OF THE DRAWINGS

FIGS. 4A through 4C illustrate an exemplary method of the present invention in which the apparatus of FIGS. 1A and 1B is used in the following manner: (A) a biological material, such as BMA, is drawn into the device thereby infiltrating the porous substrate material, (B) the plunger is depressed against the congealed mass of material and BMA, and the end piece of the device is removed to provide a biological composite and (C) the biological composite is delivered to an osseous defect site.

FIG. 5A is a side view of another exemplary delivery device of the present invention.

FIGS. 5B through 5D are additional components that are used with the device of FIG. 5A to create and deliver a biological material including a plunger 50 (FIG. 5B), vacuum adapter 100 (FIG. 5C) and a secondary syringe (FIG. 5D).

DETAILED DESCRIPTION OF PREFERRED EMBODIMENTS

The present invention relates to apparatuses for the delivery of a biological composite that house substrate materials, that allow for the materials to be rendered biologically active to form biological composites, and that facilitate delivery of biological composites to an osseous defect site. Preferably, the substrate material is a highly porous β-TCP with a pore volume of at least 70% and interconnected porosity of pore sizes that may range from less than about 1 μm to about 1000 μm or greater. In another embodiment, the substrate material is an admixture of the highly porous β-TCP with a polymer, such as collagen.

Figure 1A:
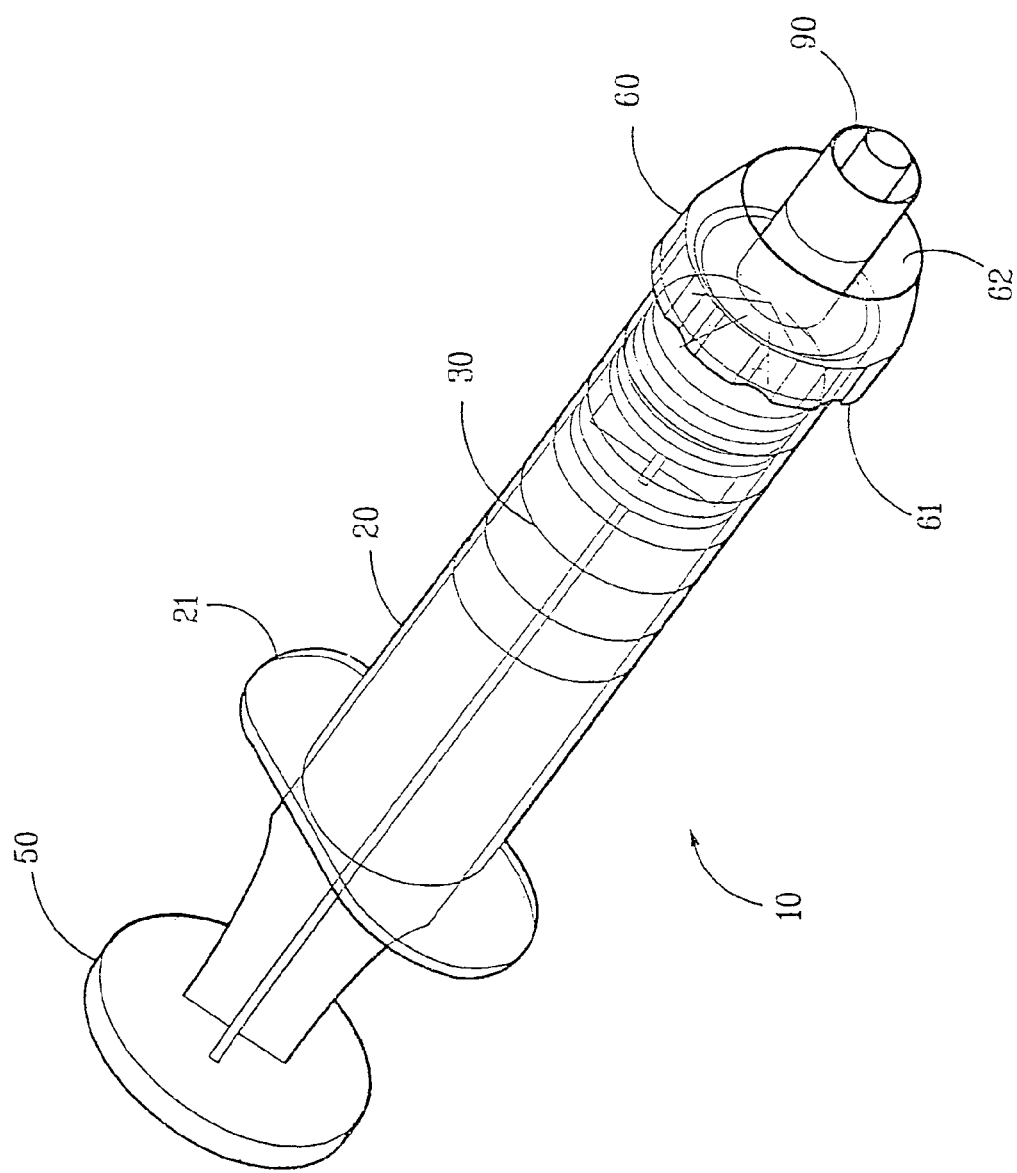
FIGS. 1A and 1B are side elevation and exploded views, respectively, of an exemplary delivery device of the present invention.
Figure 1B:
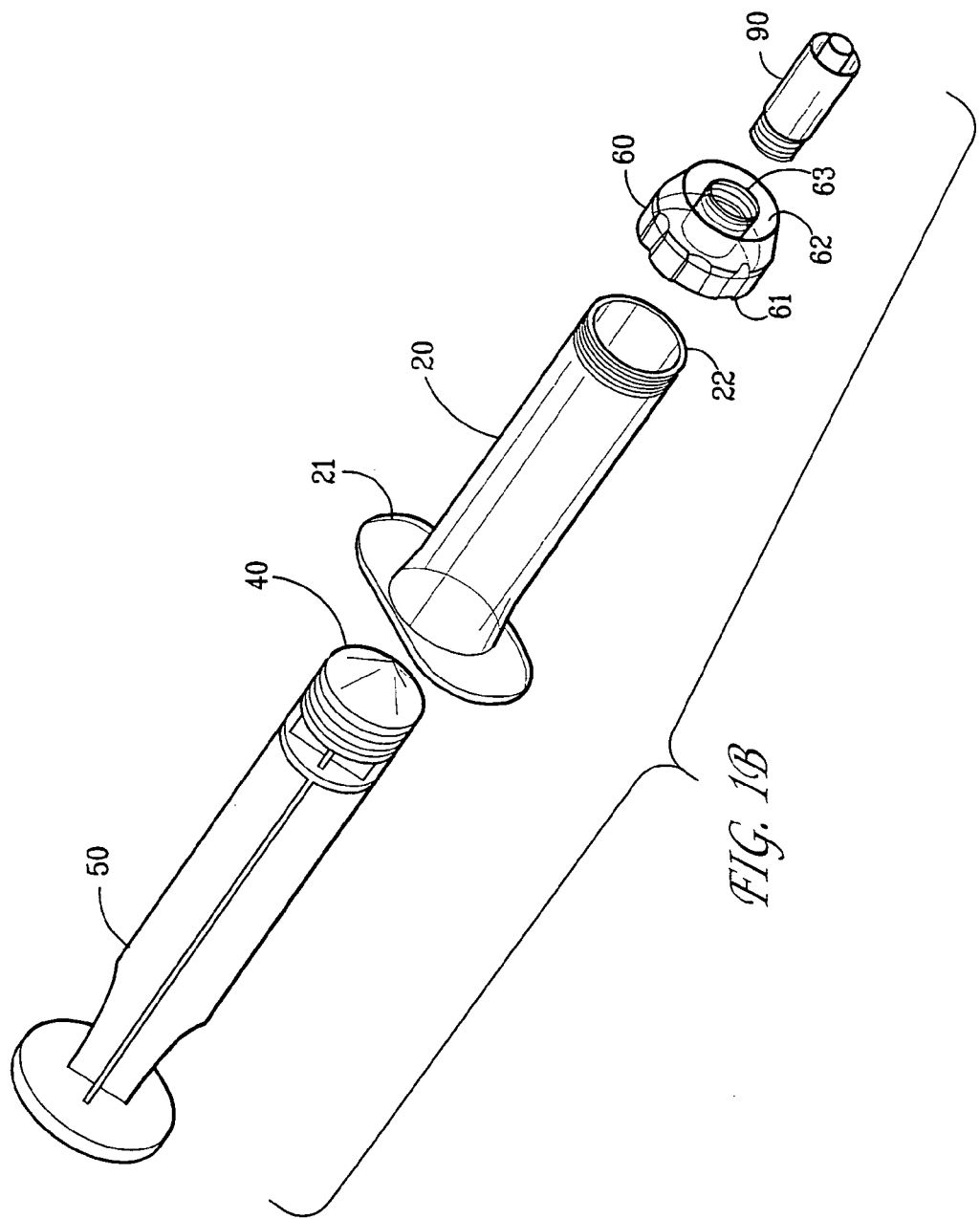
Figure 2:
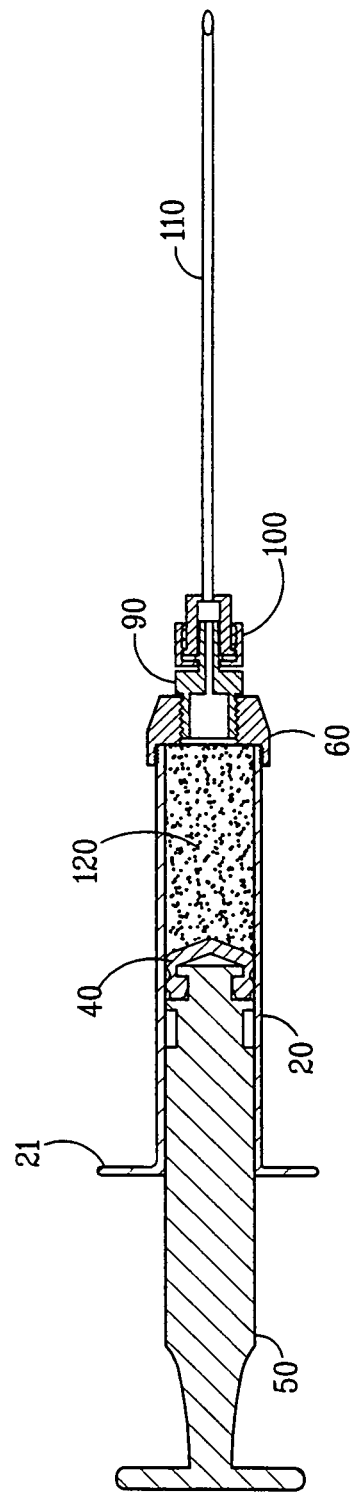
FIG. 2 is the device of FIGS. 1A and 1B, showing the morselate material housed within.

FIGS. 1A, 1B, and 2 provide one example of a presently preferred embodiment of the present invention. As these figures illustrate, apparatus 10 comprises a material chamber 20 having a proximal end 21 and a distal end 22 defining an interior chamber therein for housing a porous substrate 120 as shown in FIG. 2. In certain embodiments, material chamber 20 may be tubular or cylindrical shaped. Preferably, material chamber 20 may have external calibration markings 30 (see FIG. 1A) to measure the amount of material housed, drawn into, or aspirated within or into material chamber 20. Apparatus 10 may further include a piston or gasket 40, as shown in FIGS. 1B and 2, which may reside within the material chamber 20 and is moveable therein via engaging plunger 50 attached thereto. Plunger 50 is removable from the housing to allow for material insertion within the material chamber 20, or the injection of any desired material, such as biologic material, into chamber 20.

The distal end 22 of apparatus 10 is provided with a removable dismountable end cap 60 with a proximal end 61 having threads, guides, slots, or other structures for engaging corresponding threads, guides, slots, or other structures on the distal end 22 of the material chamber 20. Dismountable end cap 60 further includes a distal end 62 with a point for attachment 63 of an aspiration needle 110. In a preferred embodiment, the point for attachment 63 is a male Luer-lock connector 90 that threadingly engages the distal end 62 of the dismountable end cap 60 and allows for attachment of a female Luer-lock 100 situated on the end of a needle 110 for the aspiration of fluids. In other embodiments of the present invention, the male Luer-lock connector 90 is integrated with the distal end 62 of the dismountable end cap 60 (not shown). An adhesive, such as but not limited to a polyurethane adhesive, may also be used between dismountable end cap 60 and Luer-lock connector 90 to form an integrated piece. An exemplary polyurethane adhesive is Product #1187-M provided by Dymax Corporation of Torrington, Ct.

As shown in FIG. 2, material chamber 20 further includes a substrate material 120 contained therein. Substrate material 120 may be comprised of a variety of synthetic biocompatible bone materials and ceramic materials, including, but not limited to, those comprising calcium phosphate. Material 120 may be in a variety of forms such as an integral body of porous material, granules, or morsels. Preferred biocompatible materials are those obtained generally in accordance with the disclosure of U.S. Pat. No. 5,939,039 filed Jan. 16, 1997, assigned to the assignee of the present invention and incorporated herein by reference in its entirety. Such β-tricalcium materials exhibit a high degree of porosity over a wide range of effective pore sizes. Other preferred materials are composites comprising those materials described above admixed with a porous, resorbable, polymeric component such as collagen.

Figure 3:
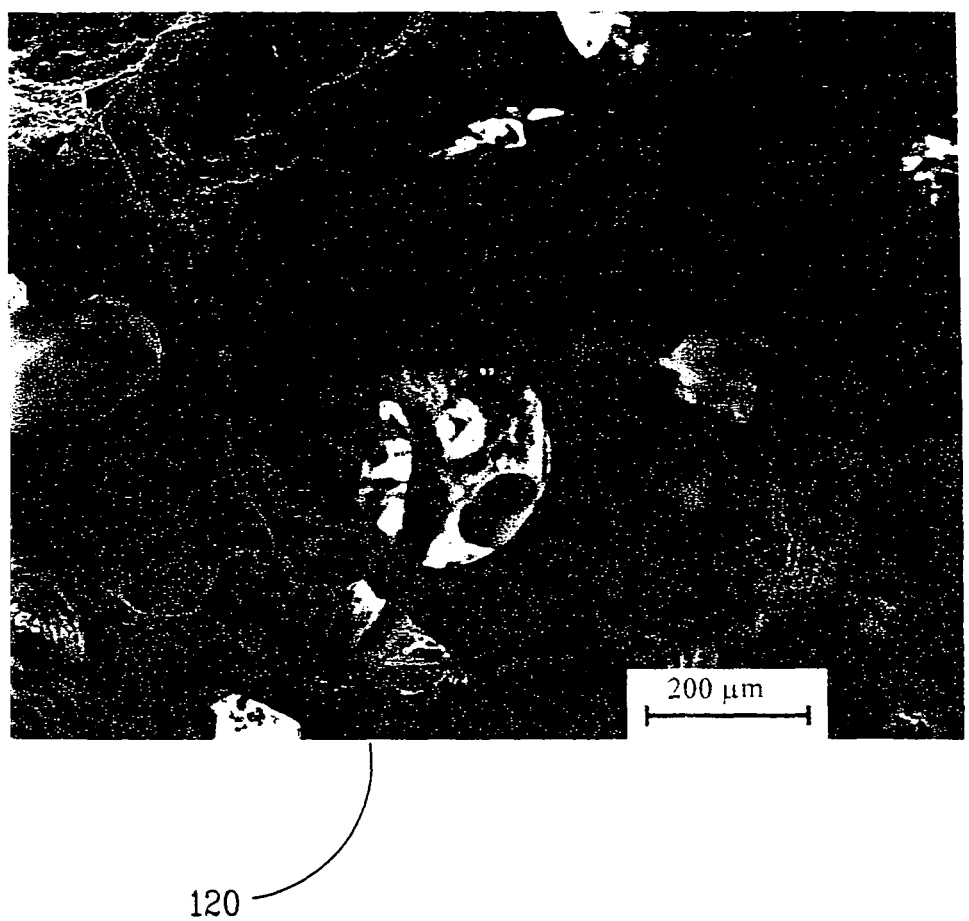
FIG. 3 is a 100×magnification scanning electron micrograph ("SEM") of an exemplary inorganic substrate material that depicts the macro-, meso-and micro-porosity contained therein.
Figure 5C:
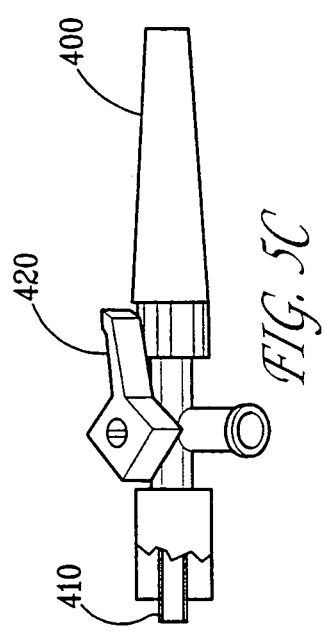
Figure 5D:
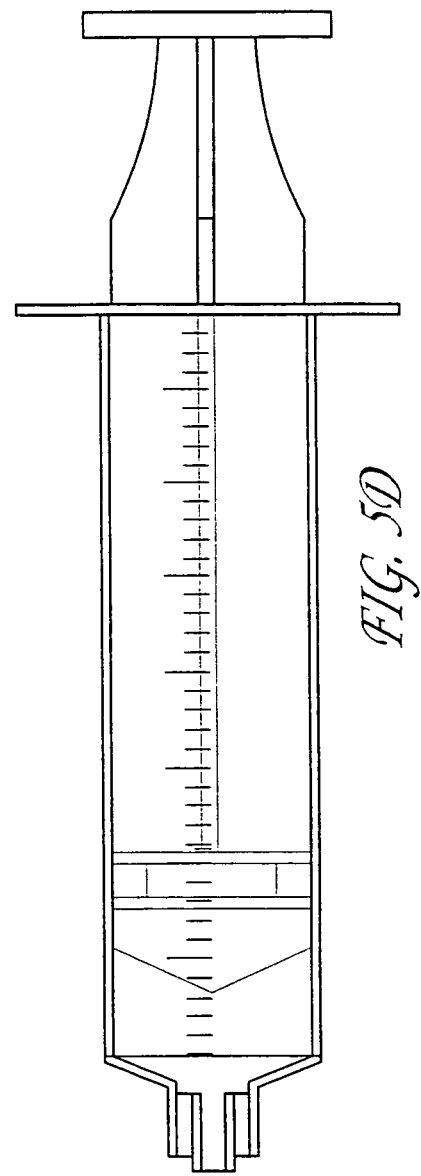
Figure 6A:
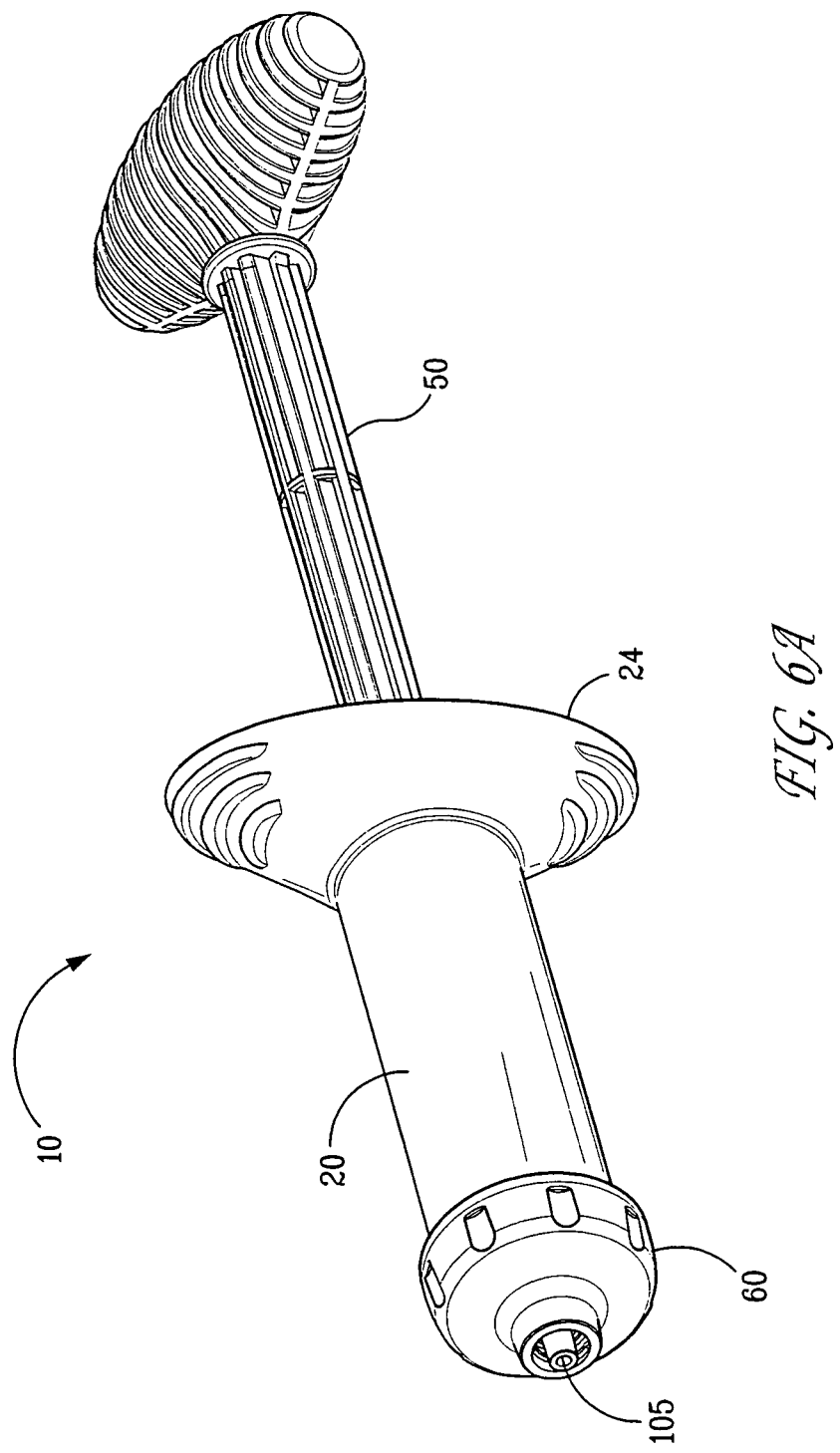
FIG. 6A is a schematic of another exemplary device of the present invention.
Figure 6B:
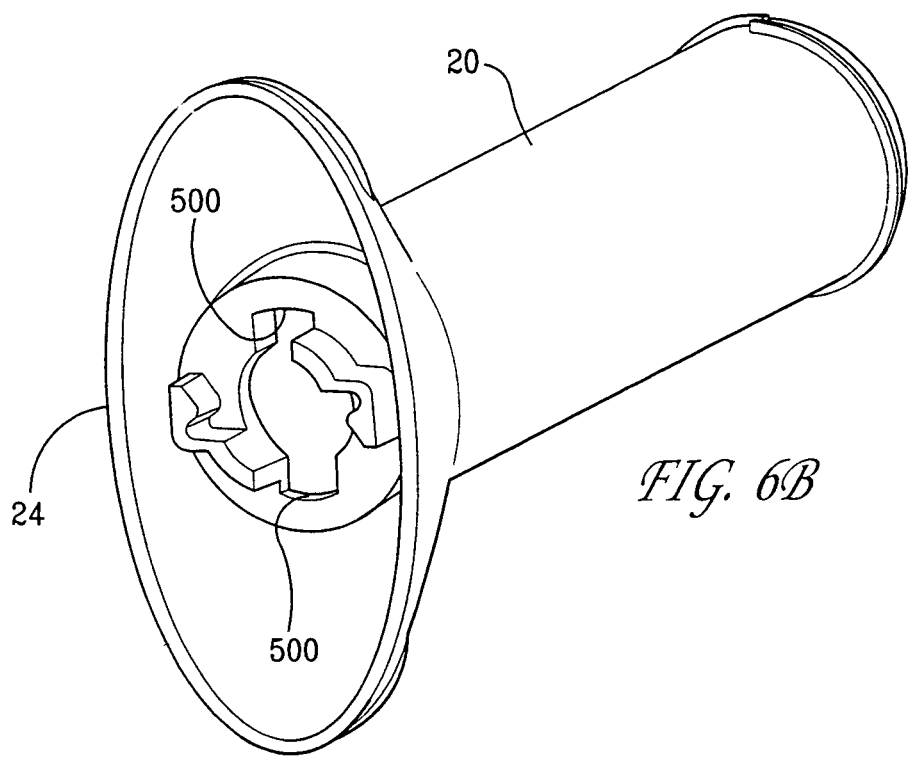
FIGS. 6B through 6H depict the individual components that comprise the device of FIG. 6A.
Figure 6C:
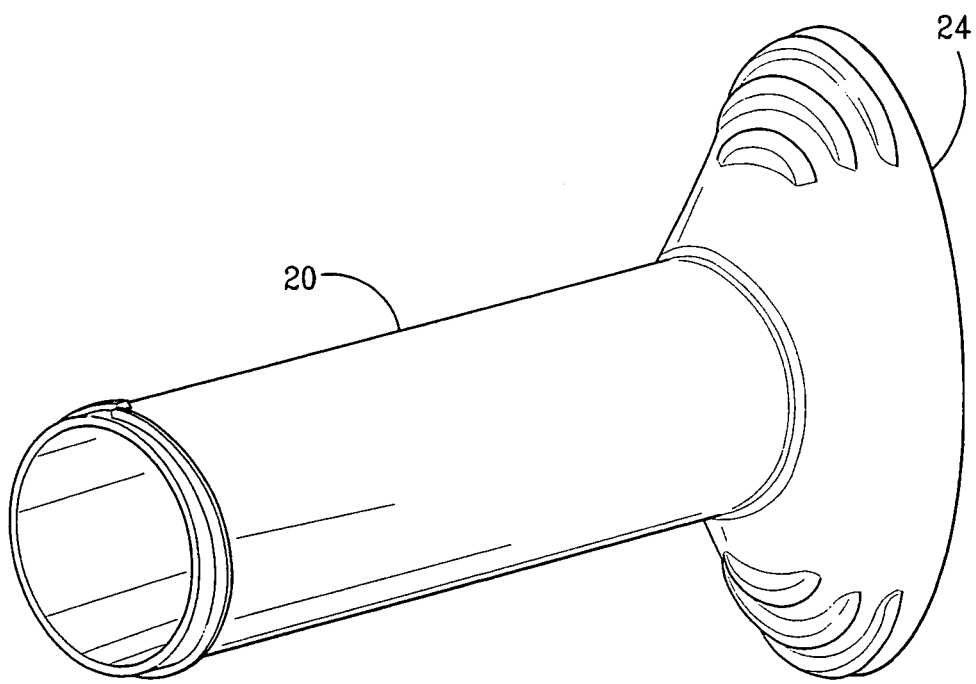
Figure 6D:
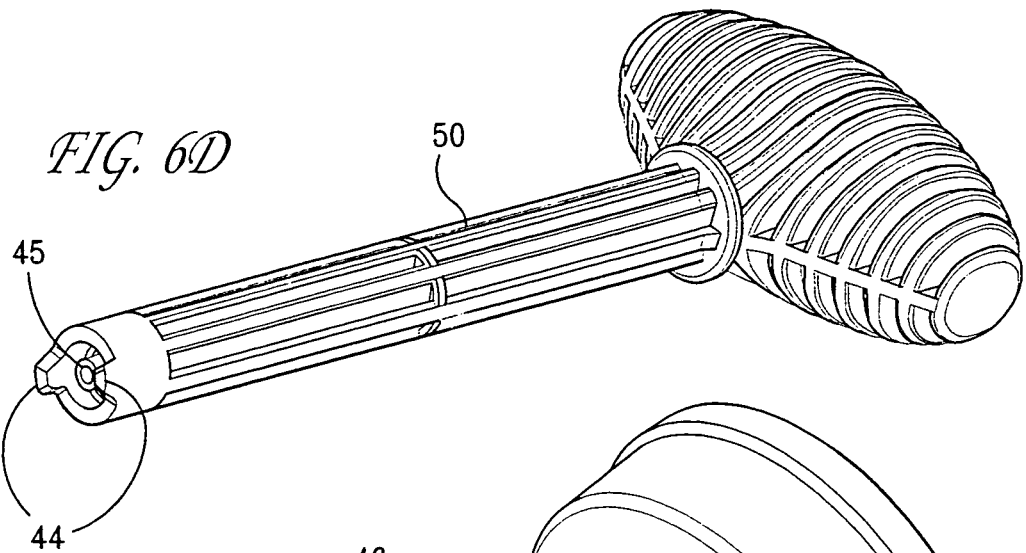
Figure 6E:
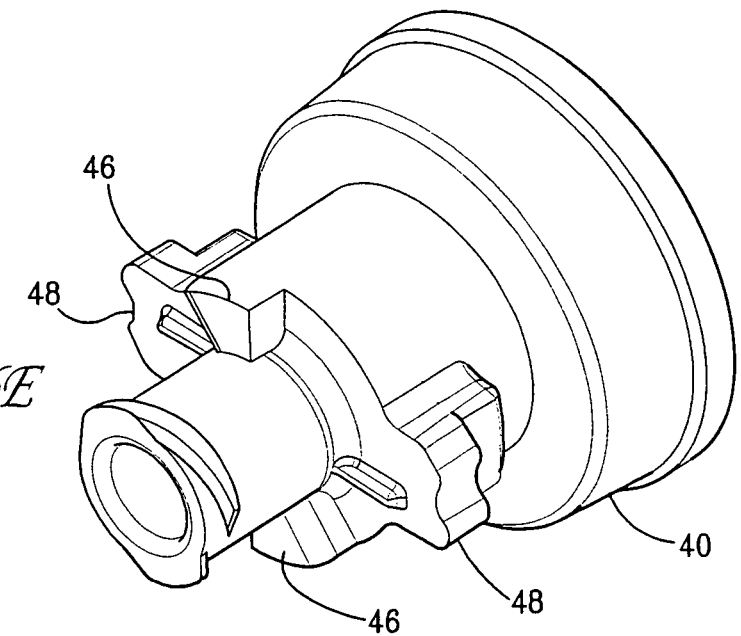
Figure 6F:
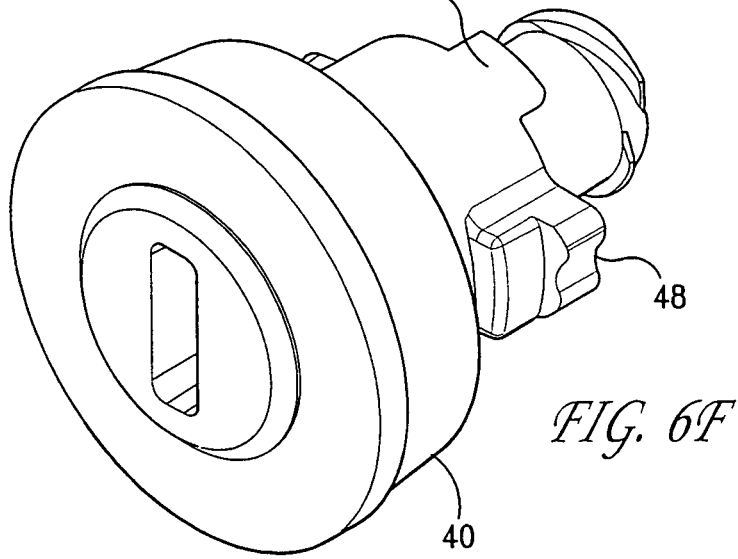
Figure 6G:
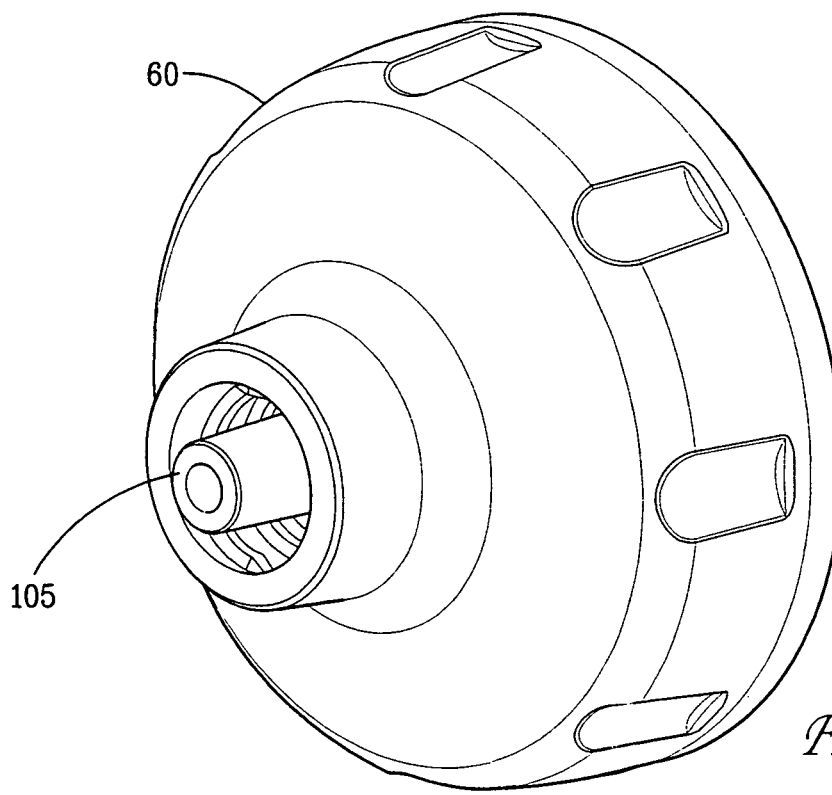
Figure 6H:
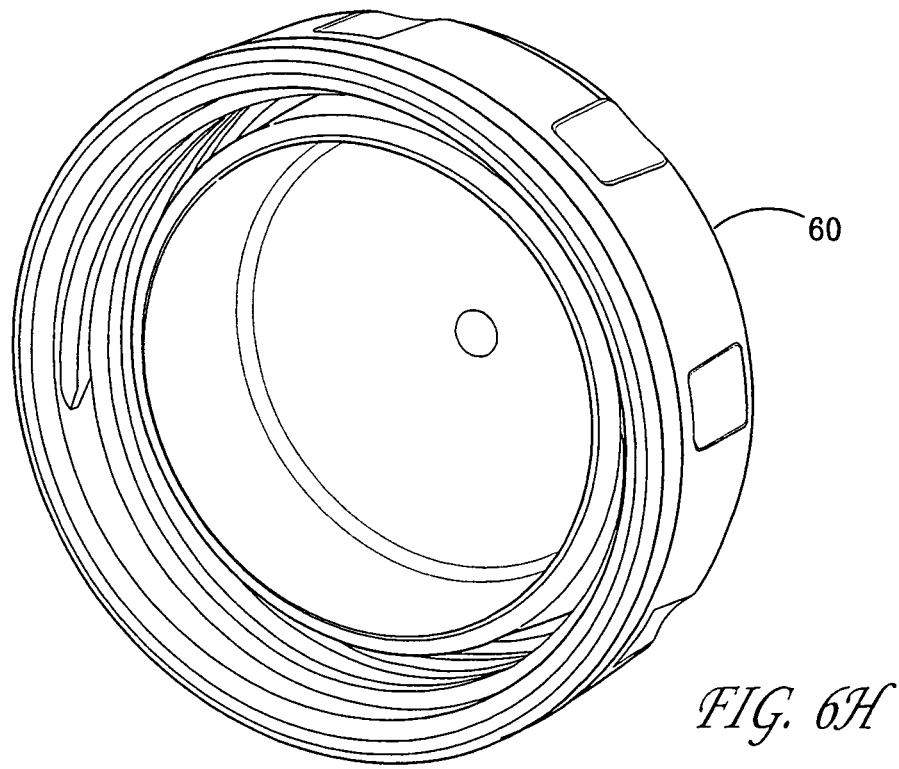

In embodiments where substrate material 120 is an integral body of porous material, the body preferably exhibits within its microstructure, a combination of macro-porosity, meso-porosity, and micro-porosity. Macro-porosity, as used herein, relates to materials characterized by pore diameters about 100 μm or greater and, in some embodiments, up to about 1000 μm or above. Meso-porosity, as used herein, relates to materials characterized by pore diameters that range from about 10 to about 100 μm. Micro-porosity, as used herein, relates to materials characterized by pore diameters below about 10 μm, and more preferably about 1 μm or below. FIG. 3 provides a SEM of the microstructure of a preferred substrate material that may be used in the present invention. It is preferred that macro-, meso-, and micro-porosity simultaneously occur in a random and interconnected nature throughout the porous substrate material used in the present invention. It is not necessary to quantify each type of porosity to a high degree. Rather, persons skilled in the art can easily determine whether a material has each type of porosity through examination, such as through the SEM or other methods known in the art.

In addition to the interconnected range of pore sizes, porous substrate material 120 may have pore volumes of at least about 70% or greater, preferably about 85% or greater, and even more preferably about 90% or greater. Such high pore volumes may be achieved while also maintaining the presence of macro-, meso-, and micro-porosity within the microstructure and physical stability of the materials produced. These aspects of the porous substrate material are desirable for use within the apparatuses, kits, systems, and methods of the present invention in that they facilitate wicking of the biological material and infiltration of the viable components of the biological fluid.

In preferred embodiments of the present invention, porous scaffold material 120 may comprise a tri-calcium phosphate such as β-TCP. In addition to the array of desirable features discussed above, porous scaffold material comprising β-TCP may be resorbable. The composition, physical structure and solubility of the implant may strongly influence the resorption of calcium-based bone implants. The preferred porous bodies have significant resorption due to their low density, high porosity, nano-size particle composition, and chemistry.

As calcium-based implants are resorbed, they are often replaced by new bone. Porous tri-calcium phosphate bone implants resorb more quickly than porous hydroxyapatite, with their resorption rate being concurrent with a rapid rate of in-growth and remodeling of new bone if the structure of the implant is appropriate. The porous scaffold material may also be a composite of β-TCP with another resorbable material such as collagen. It should be understood that such composite would also have a high porosity and broad pore size distribution.

The infiltrant in the present invention can be a number of substances that render the porous material bioactive including, but not limited to, biological materials such as bone marrow, whole blood, plasma, or other blood components or growth factors, but preferably contains one or more components of BMA. BMA is a complex tissue comprised of cellular components (that contribute to bone growth) including red and white blood cells, their precursors and a connective tissue network termed the stroma. Bone marrow stromal cells or mesenchymal stem cells have the potential to differentiate into a variety of identifiable cell types including osteoblasts, fibroblasts, endothelial cells, reticulocytes, adipocytes, myoblasts and marrow stroma. Consequently, bone marrow aspirate is a good source of osteogenic cells for immediate transplantation. For subsequent use in transplantation, stem cells can also be cultured and expanded many times to increase their original number. Stromal cells regulate the differentiation of hemopoietic cells through cell-surface protein interactions and secretion of growth factors. Bone marrow may be used to stimulate bone healing in many applications providing a promptly renewable, reliable source of osteogenic cells. BMA may also provide osteogenic components, namely the progenitors of osteoblasts.

Thus, the present invention device is provided with means for preparing and delivering a biological composite that may be osteoconductive, osteogenic and osteoinductive. In certain embodiments, the tri-calcium phosphate materials of the type disclosed herein have been shown to function as osteoconductive bone graft scaffolds. With the addition of aspirated BMA into the ultraporous β-TCP scaffold material to form a biological composite, the resultant material may become osteogenic and osteoinductive. The osteogenic and osteoinductive potential is further enhanced due to the interconnected porosity of the material which facilitates infusion of bone matrix proteins and growth factors. Osteogenic cells can also migrate into the open architecture of the scaffold and mingle with the seeded bone-forming cells, thereby enhancing the osteogenic properties of the β-TCP.

The present invention finds utility in a wide variety of applications and may provide an alternative to autografts, or implantation materials comprised of cadaver bone, bovine bone, or the like. The porous scaffold material and biological composite formed therein can be used in medicine, such as, but not limited to, the restoration of bony defects. The materials can also be used for the delivery of medicaments that are internal to the defect. In this way, the pores of the substrate can be partially filled with another material which either comprises or carries a medicament such as a growth hormone, antibiotic, cell signaling material, or the like. Indeed, the larger porous spaces within some of the products of the present invention can be used for the culturing of cells within the human body. In this regard, the larger spaces are amenable to the growth of cells and can be permeated readily by bodily fluids such as certain blood components. In this way, growing cells can be implanted in an animal through the aegis of implants in accordance with the present invention. These implants can give rise to important biochemical or therapeutic or other uses.

In a preferred embodiment of the present invention, the apparatus is used to prepare a biological composite using the method and kit depicted in FIGS. 4A, 4B and 4C. As these figures illustrate, plunger 50 or dismountable end cap 65 is removed from apparatus 10 and the biocompatible material 120 is inserted into material chamber 20. Dismountable end cap 65 is an integral piece that comprises Luer-lock connector 95. Luer-lock mating means 105 with needle attachment 110 may be connected thereto. Plunger 50 is then reinserted into, or dismountable end cap 65 is placed back onto, material chamber 20. Piston 40 is displaced so that it abuts and lightly packs the material (not shown). The tip of the biopsy needle 110 is then inserted into an appropriate anatomical site 130, such as for example the iliac crest. Biopsy needle 110 preferably has a solid trochar (not shown). The syringe is then connected to needle 110 via the Luer-lock mating means 105 and connector 95. Withdrawal of the plunger creates a vacuum within the housing 20, which allows for the biological fluid to be drawn into the housing of the device as shown in FIG. 4A. The fluid completely imbibes and infiltrates the biocompatible material 120, once in contact with the material, by virtue of its highly porous and interconnected porosity. The plunger is depressed so that it abuts and compacts both the material and infiltrate so that the two are allowed to coagulate within the housing to form a biological composite 140 having an improved handling consistency and osteogenic potential. As FIG. 4B shows, the resulting composite 140 behaves as a unit mass and can be surgically implanted via displacement of the plunger 50, upon removal of the dismountable end cap 65. A wrench (not shown) may be used that mates with dismountable end cap 65 to aid in opening and closing the syringe. In other embodiments of the method of the present invention, material chamber 20 may be pre-filled with BMA or another biocompatible material and dismountable end cap 65 or plunger 50 may be removed to insert substrate material 120.

Disclosed here are also apparatuses for preparing a biological composite, comprising a plunger 50 having tabs 44 for mating; a material chamber 20, having a proximal end 21 and a distal end 22, and comprising a calcium phosphate material having macro-, meso- and micro-porosity, the proximal end 21 having a piston 40, which sits proximally within the handle of the material chamber 20 for mating with said plunger 50; and the distal end 22 of the chamber 20 being closed by a dismountable end cap 60, an end cap 60 being provided with a point for attachment for an aspiration needle. The apparatuses may further comprise two seals located on either end of said material chamber 10 adjacent to said piston 40 and said end cap 60.

As shown in FIGS. 5A-5D, the apparatus 10 may comprise a material chamber 20 having a proximal end 21 and a distal end 22. The promial end 21 is sealingly closed by a moveable piston 40. The material chamber 20 may house or contain a biocompatible material or substrate 140. The proximal end 21 further comprises a handle 24 which may be threaded or glued onto the chamber 20. The handle 24 houses a piston 40 having an adaptor 47, such as a Luer adaptor, which may be capped with a cap-like plug 91 at a first end. The piston 40 may include a hex net centrally, and/or locking tabs at a second end. The second end may be positioned within the handle 24 adjacent the material chamber 20. The distal end 22 of the apparatus 10 further comprises a dismountable end cap 60. The end cap 60 may be threaded or snapped-on to the material chamber 20 and may include a mechanism for attachment 105, such as a cap Luer, and may include a cap plug 94. When the apparatus is used, the plunger 50 is mated with the adaptor 47 of the piston 40. The plunger may include a built-in hex socket to assist in mating with the hex nut of the piston 40. In some embodiments, the piston 40 may be in a locked position to prevent premature release of the material. Mating the plunger 50 with the adaptor 47 may serve to unlock the piston 40 for discharging the material 140 from the chamber 20. Depending upon the embodiment of the apparatus, the unlocking may be performed through rotating the piston 40 with the mated plunger 50. Both piston 40 and plunger 50 now may slide down mating grooves or keyways 500. Since the push rod 50 is mated with the adaptor 47, the piston 40 does not fall into the surgical site after the graft is expelled.

Certain embodiments further comprise a number of seals. A first seal may be located between the piston 40 and the handle 24; a second seal may be located between the end cap 60 and the material chamber 20. In some embodiments the seals are on either end of the material chamber 20 adjacent to the piston 40 and the dismountable end cap 60. The seals insure that material 140 housed within the chamber 20 is kept dry. The seals prevent leakage of blood or bone marrow aspirate that may be aspirated into the chamber and facilitate the draw of a vacuum when desired. The apparatus 10 may also include a gasket at the handle opening. This gasket provides a safety seal during attachment of a secondary syringe 300, to the adaptor 47. The gasket may also prevent the piston from loosening when the syringe is placed onto the adaptor 47 and may provide an additional seal for vacuum.

Another embodiment comprises attaching a secondary syringe 300 to the adaptor 47 and using the plunger of the secondary syringe 300 to draw a vacuum to aspirate fluids. An embodiment that may be preferred comprises attaching a secondary syringe 300 that already contains a biologic fluid, to the adaptor 47 and injecting the fluid into the material chamber 20. In yet another embodiment, a vacuum adapter 100 is attached to the adaptor 47 at the proximal end 21 of the material chamber 20.

If the embodiment has a vacuum adaptor 400, the flow of the vacuum flow may be controlled by whatever means suitable for the chosen adaptor. For example, certain adaptors may allow for rotating a valve handle 420 to prevent vacuum flow through the adapter 400; connecting the adapter 100 to the vacuum line in the surgical suite; opening the valve 420 to apply suction; then, after collecting the desired amount of fluid, rotating the valve handle 420 to stop suction. In this embodiment, a needle may be attached by way of the distal adaptor 105 in the cap and is either in the harvest site for bone marrow aspirate harvest or in a blood line.

In certain methods, once the desired volume of autogenous blood or bone marrow has been collected, the needle is removed from the apparatus 10 and discarded. The secondary syringe 300 or vacuum adapter 100 is also removed. The plunger 50 is then attached to the piston adaptor 47 at the proximal end 21 of the apparatus 10. In some embodiments, the plunger 50 engages the piston 40 and rotates the piston 40 to unlock it. The dismountable end cap 60 is then removed from the distal end 22 of the material filled apparatus 10, and the plunger 50 is used to expel the bone void filler/bone graft material 20 out of the material chamber 20. Material can be delivered directly to the surgical site or may be expressed in a sterile bowl to be used at the surgeon's discretion.

In an alternate embodiment 10 as depicted in FIGS. 6A-6H, the handle assembly 24 may be integrally formed with the material chamber 20. The handle assembly 24 includes a piston 40 with an adaptor 47, tabs 46, and wings 48. The apparatus 10 also includes a plunger 50 with an adaptor 45 and tabs 44. The adaptor 45 and tabs 44 of the plunger 50 engage the adaptor 47 and tabs 46 of the piston 40. This engagement unlocks the piston 40. The piston 40 may then be moved to expel the material from the chamber 20 into the site. The dismountable end cap 60 is removed to allow the biocompatible material to be expelled from the material chamber. In some embodiments, the wings 48 of the piston 40 fit within and slide down the built in keyways 500 of the handle assembly 24 and allow the plunger 50 to traverse the chamber 20 and expel the material upon removal of the dismountable end cap 60.

As described above, embodiments of the present invention may be used to prepare a biologic composite via direct or indirect aspiration methods. For bone marrow collection, a bone marrow needle may be inserted into a desired harvest site using standard aseptic techniques. For blood collection, a venipuncture may be used to access a central blood line using standard aseptic techniques. The direct aspiration method comprises connecting the apparatus 10 to a needle via an adaptor 105 or other suitable connecting means. At the proximal end of the apparatus 10, a secondary syringe 300 having a greater or equal volume to the material chamber 20 of the apparatus 10 is attached via an adaptor 47. The desired amount of blood, marrow, or blood component is then aspirated into the material chamber 20 of the apparatus 10 by applying suction with the secondary syringe 300. The desired amount of blood, marrow, or blood component is then mixed with the substrate material housed in the material chamber 20 as the aspiration proceeds. Once aspiration is complete, the secondary syringe 300 may be removed. The resultant composite may then be placed into a bony void by removing the dismountable end cap 60 and extruding the composite by applying force to the engaging plunger 50.

The present invention may also be used to prepare a biologic composite via an indirect aspiration method. A bone marrow needle may be inserted into a desired harvest site via standard techniques. A secondary syringe 300 is then attached to the needle and the desired amount of blood, marrow, or blood component is then aspirated into the secondary syringe 300. The filled syringe 300 is detached from the needle and then connected to the proximal end of the apparatus 10 via an adaptor 47. The blood, marrow, or blood component is then injected into the apparatus 10 to mix with the substrate material housed within the chamber 20. After coagulation, the resultant composite may then be placed into a bony void by removing the dismountable end cap 60 and extruding the composite by applying force to the plunger 50 that is engaged with the piston 40.

Aspiration may also be achieved by vacuum line aspiration. In this method, the apparatus 10 is connected to the needle that has access to bone marrow or a blood line at the distal end. At the proximate end, a vacuum line adapter 400 is attached via an adaptor 47. The desired volume of blood is then aspirated by applying vacuum pressure using the vacuum line.

It will be appreciated that the apparatuses disclosed give rise to methods for preparing a biological composite. Certain embodiments of these methods comprise the steps of:

providing an apparatus comprising a pushrod having tabs for mating; a material chamber, having a proximal end and a distal end, and comprising a calcium phosphate material having macro-, meso- and micro-porosity, the proximal end having a piston for mating with said pushrod; the distal end of the chamber being closed by a dismountable end cap, an end cap being provided with a point for attachment for an aspiration needle;

placing the aspiration needle into a situs of bone marrow or blood pathway;

attaching the aspiration needle to the dismountable end cap;

drawing a vacuum in the material chamber to cause aspiration of bone marrow or blood into the material chamber in an amount sufficient to substantially wet the biologically compatible material to form a biologically compatible composite; and maintaining the aspirate in contact with the biologically compatible composite under conditions effective to cause at least partial coalescence of the marrow within the composite.

The composite 140 can be packed into a bony void to create good contact with available bony surfaces. The resultant composite is sufficiently self-supporting to be handled manually or with surgical hand tools such as spatulas and knives. The composite need not be entirely stiff but can tend to flow under force. Suitable polymers may include structural proteins such as collagen. The biologically compatible material may have a pore volume of at least 70%. When collagen is used, 70% may be the preferred porosity of the biocompatible material. Preferably, a shapeable portion of the composite is placed into a void 150 in a bone 160 as shown in FIG. 4C. Any remaining biological composite 140 can be preserved in a freezer or other suitable means of preserving.

It should be understood that as an alternative to BMA, or in conjunction therewith, other infiltrants such as separated fractions of BMA, venous blood, one or more fractions of venous blood, thrombin, or any mixture of such or other relevant fluids can be used in the present invention. Replicated bone marrow or other types of bioengineered bone marrow material can also be used in this invention. Still further non-limiting fluids can be used or added are culture-expanded cells or solutions containing medicaments. Such fluids should improve the handling characteristics of the scaffold and impart a beneficial biological function by the nature of the fluid chosen.

The present invention also gives rise to a method and a kit that is unique in its ability to prepare and deliver the biologically active composite. A preferred kit embodiment is comprised of an apparatus or delivery device capable of holding porous, biocompatible material as described herein and a separate sterile package holding the inorganic (or inorganic-organic) material. The kit is used to prepare a biologically active composite wherein BMA or other infiltrant is absorbed into the porous material by the aspiration process. The composite is formed within the barrel of the syringe once the aspirate coagulates with the porous material. Coagulation may be assisted by the porosity of beta-tricalcium phosphate. Such biocompatible material may have up to 85% porous. The same kit can be used to deliver the resultant composite by removing the end of the syringe and extruding the composite to be placed into an osseous void. In a preferred embodiment, the material is already housed within the apparatus.

The materials, which comprise the syringe, can a variety of standard polymeric materials used in the field. For instance, the material chamber or barrel and threaded dismountable end cap may be comprised of a polycarbonate material, such as that sold by Dow, 2081-15-FC030004 or polypropylene; the plunger may be comprised of acrylonitrile-butadiene-styrene (such as the Dow Magnum® 9010 material) or polypropylene; the piston may be comprised of silicone or polypropylene; the gaskets may be comprised of a silicone-64 Shore A durometer base material, such as the blend of STI-5 and TR-70 sold by Dow Corning®; a lubricant between the inside of the barrel and the plunger piston is preferably silicone oil (such as Dow Corning® Silicone 360); and the adhesive on the threaded coupling between the Luer-lock and dismountable end cap may be medical grade silicone or a number of acceptable adhesives including, but not limited to, cyanoacrylate, hot melt adhesives, or cellulosic binders. Alternatively, the Luer-lock and dismountable end cap may be integrally formed via ultrasonic welding, spin welding, or insert molding rather than the use of adhesive.

Additional objects, advantages, and features of this invention will become apparent to those skilled in the art upon examination of the following examples thereof, which are not intended to be limiting.

EXAMPLES

Example 1

Preliminary Evaluation of a Syringe System for the Aspiration of Bone Marrow, Whole Blood, Plasma of Other Blood Components in a Non-Human Primate Model A kit of the present invention for the aspiration of bone marrow, whole blood, plasma or other blood components was evaluated using a non-human primate animal model. The kit was evaluated for collection of bone marrow and venous blood, with and without a highly porous calcium phosphate scaffold material, in the following manner.

A single skeletally mature baboon was anesthetized for the duration of the study using isoflurane inhalation.

A 20-gauge needle was affixed to a male Luer-lock adaptor situated on the end of the syringe system. An 18-gauge catheter was placed in the right lateral saphenous vein of the animal for repeated blood collection, then the 20 gauge needle was placed in contact with the 18 gauge catheter for collection of venous blood. The ability of the syringe system to draw blood was subjectively evaluated with and without the addition of 5 cc of a morselate calcium phosphate material in the material chamber of the syringe. This evaluation was compared a Luer Lock 10 cc disposable syringe, manufactured by the Becton Dickinson Co. of Rutherford, N.J., with the addition of 5 cc of the morselate calcium phosphate material described above.

Following venous blood collection, the syringe system was evaluated during harvest of bone marrow aspirate from the posterior superior iliac spine region of the right ileum using an 11-gauge Jamshidi needle was placed directly in the site the syringe system was and then attached for aspiration. The ability of the syringe system to aspirate bone marrow was subjectively evaluated with and without the addition of 5 cc of a morselate calcium phosphate material in the material chamber of the syringe.

The syringe system, both with and without the addition of 5 cc of a morselate calcium phosphate material in the material chamber, was sufficient for both collection of venous blood and the harvest of bone marrow aspirate. Adding the porous material to the chamber had no effect on the ability of the system to draw blood or aspirate marrow. The vacuum that was generated in each case was sufficient. There were no differences between a first draw of blood with the syringe system in comparison with a second draw from the same syringe.

Example 2

Healing of Tibial Segmental Defects in Dogs Using Biologically Active Composites Thirty-five vials of a porous, biocompatible material such as VITOSS™ Scaffold Synthetic Cancellous Bone Void Filler morsels (provided by Orthovita of Malvern, Pa.), referred to herein as "Test Articles" were prepared and assigned a unique identification number for the study. Table I provides the animal subjects' ID number, test article ID numbers, amount of biological material imbibed into the VITOSS™ porous scaffold material, and the amount in grams of the residual VITOSS™ and BMA composite.

TABLE I

| Animal ID | Test Article ID | Amount Mixed (g) | Residual VITOSS ™/BMA (cc) |
|---|---|---|---|
| 11A | ORL-131-T | 0.72 | 0.9 |
| 11B | ORL-101-T | 0.54 | 0.3 |
| 11C | ORL-117-T | 0.72 | 1.0 |
| 11D | ORL-131-T | 0.80 | 0.7 |
| 11E | ORL-109-T | 0.37 | 0.4 |
| 12A | ORL-134-T | 0.79 | NA |
| 12B | ORL-119-T | 1.04 | NA |
| 12C | ORL-101-T | 1.21 | NA |
| 12D | ORL-109-T | 0.45 | NA |
| 12E | ORL-127-T | 1.15* | 3.0* |
| 13A | ORL-113-T | 0.76 | 0.2 |
| 13B | ORL-113-T | 0.85 | 0.3 |
| 13C | ORL-119-T | 0.77 | NA |
| 13D | ORL-118-T | 0.94 | 0.3 |
| 13E | ORL-131-T | 0.88 | 0.6 |
| 14A | ORL-134-T | 0.86 | 0.3 |
| 14B | ORL-118-T | 1.61* | NA* |
| 14C | ORL-100-T | 0.93 | NA |
| 14D | ORL-133-T | 0.79 | NA |
| 14E | ORL-133-T | 0.97 | NA |
| 15A | ORL-113-T | 0.79 | NA |
| 15B | ORL-134-T | 0.83 | 0.4 |
| 15C | ORL-133-T | 0.75 | 0.1 |
| 15D | ORL-131-T | 0.84 | 0.5 |
| 15E | ORL-109-T | 0.74 | NA |
| 16A | ORL-134-T | 0.73 | NA |
| 16B | ORL-119-T | 0.81 | NA |
| 16C | ORL-117-T | 0.75 | NA |
| 16D | ORL-117-T | 1.05 | NA |
| 16E | ORL-127-T | 0.90 | NA |

*An additional quantity of VITOSS ™/BMA was prepared for use if necessary.

Surgical procedures were scheduled in "sessions", with three surgical procedures typically performed per session. Prior to the start of each surgery session, a vial of the Test Article was removed from the sterile packaging for use during the entire session. Care was taken to maintain sterility of the vial throughout the session.

While maintaining sterility, each vial of Test Article was weighed prior to, and following, removal of material for placement in each Test System. The total amount of Test Article used in each Test System was determined in this way.

Prior to the first surgical procedure, the method for preparing and mixing the Test Article was determined in the following manner:

1. A 5 cc syringe was filled to the 4 cc mark with Test Article.
2. The syringe was tapped to settle the Test Article.
3. The syringe plunger was then compressed to the 3 cc mark.
4. The syringe containing the Test Article was attached to the needle being used for BMA collection.
5. BMA was either: (1) drawn into the syringe through the Test Article such that it completely saturated it; or (2) drawn into a 1 cc syringe and then transferred to the 5 cc syringe containing the VITOSS™ scaffold material such that the BMA completely saturated it. In some instances, the syringe was removed to withdraw air and reattached.
6. Following saturation, the plunger was compressed to the 3 cc mark.
7. The syringe containing the mixture was allowed to sit for at least 5 minutes.
8. The tip was removed from the syringe so that the mixture could be removed.
9. The mixture was placed into the defect and finger packed.

Thirty animals underwent an identical surgical procedure. Surgery was performed in accordance with the following study protocol. The experimental hind limb was prepped and draped in standard sterile fashion. The lilac crest was exposed laterally through a 2 cm or smaller skin incision and BMA was collected using a 13 or 15 gauge Jamshidi needle and syringe. The BMA was then mixed with the VITOSS™ scaffold material to provide a biological composite. At least 3 cc of BMA was collected from the animal for mixing. The amount of VITOSS™ scaffold material that was mixed with the BMA is provided in Table I.

Following closure of the marrow harvest site, a four-pin, Type 1 Kirschner external fixator was placed on the anteriolateral aspect of the experimental tibia. A medial skin incision approximately 3 cm in length was made and exposure of the tibia was obtained using sharp and blunt dissection. Once exposed, the periosteum was scored and reflected back. The major axis of the mid-section of the tibia was then measured. A cortical segmental defect approximately two times the mid-shaft major axis dimension was created in the mid-tibia using an oscillating saw. The defect was then completely filled with the VITOSS™ scaffold material with BMA and the periosteum closed with a non-absorbable suture to contain it. The residual amount of remaining biological composite after the defect was filled is shown in Table I. The soft tissues were closed in layers.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claim:

1. An apparatus for preparing a biological composite, comprising:
   a material cartridge comprising a chamber, essentially free of added anti-coagulant, having a proximal end and a distal end and, within the chamber, a biocompatible material comprising calcium phosphate material having interconnected macroporosity, mesoporosity, and microporosity, the proximal end of the chamber being sealingly closed by a piston; and
   the distal end of the chamber being closed by a dismountable end cap, the end cap being provided with a point for attachment of an aspiration needle
   wherein the biological composite comprises the biocompatible material and coagulated biological fluid comprising bone marrow aspirate.

2. The apparatus of claim 1 further comprising a closed end cap that is interchangeable with the dismountable end cap for sealing the material chamber between the piston and the closed end cap.

3. The apparatus of claim 1 wherein said calcium phosphate material has a porosity of at least 85%.

4. The apparatus of claim 1 wherein said calcium phosphate material has a porosity of at least 88%.

5. The apparatus of claim 1 wherein said calcium phosphate material has a porosity of at least 90%.

6. The apparatus of claim 5 wherein said calcium phosphate comprises β-tricalcium phosphate.

7. The apparatus of claim 1 wherein the point for attachment is a Luer lock connector.

8. The apparatus of claim 1 wherein said calcium phosphate material is combined with collagen.

9. The apparatus of claim 1 wherein the macroporosity of the biocompatible material is characterized by a pore diameter ranging from about 100 μm to about 1000 μm or greater, the mesoporosity is characterized by a pore diameter ranging from about 10 μm to about 100 μm, and the microporosity is characterized by a pore diameter below about 10 μm.

10. An apparatus for preparing a biological composite, comprising:
   a) a plunger having tabs for mating;
   b) a material cartridge comprising a chamber, essentially free of added anti-coagulant, having a proximal end and a distal end and, within said chamber, a biocompatible material comprising collagen and having interconnected macroporosity, mesoporosity, and microporosity, the proximal end having a piston for mating with said plunger;
   c) the distal end of the chamber being closed by a dismountable end cap, the end cap being provided with a point for attachment of an aspiration needle
   wherein the biological composite comprises the biocompatible material and a coagulated biological fluid comprising blood or bone marrow aspirate.

11. The apparatus of claim 10 further comprising two seals located on either end of said material chamber adjacent to said piston and said end cap.

12. The apparatus of claim 10 wherein said biocompatible material has a porosity of at least 70%.

13. The apparatus of claim 10 wherein said biocompatible material has a porosity of at least 85%.

14. The apparatus of claim 10 wherein said biocompatible material has a porosity of at least 88%.

15. The apparatus of claim 10 wherein said biocompatible material has a porosity of at least 90%.

16. The apparatus of claim 10 wherein said biocompatible material comprises calcium phosphate.

17. The apparatus of claim 16 wherein said calcium phosphate comprises β-tricalcium phosphate.

18. The apparatus of claim 10 wherein said calcium phosphate material is combined with collagen.

19. The apparatus of claim 10 wherein the interconnected macroporosity of the biocompatible material is characterized by a pore diameter ranging from about 100 μm to about 1000 μm or greater, the mesoporosity is characterized by a pore diameter ranging from about 10 μm to about 100 μm, and the microporosity is characterized by a pore diameter below about 10 μm.

* * * * *